US011188589B2

(12) United States Patent
Bruce et al.

(10) Patent No.: US 11,188,589 B2
(45) Date of Patent: Nov. 30, 2021

(54) ASSOCIATING RECEIVED MEDICAL IMAGING DATA TO STORED MEDICAL IMAGING DATA

(71) Applicants: Richard James Bruce, Verona, WI (US); Gary John Wendt, Middleton, WI (US)

(72) Inventors: Richard James Bruce, Verona, WI (US); Gary John Wendt, Middleton, WI (US)

(73) Assignee: WITS(MD), LLC., Madison, WI (US)

( * ) Notice: Subject to any disclaimer, the term of this patent is extended or adjusted under 35 U.S.C. 154(b) by 297 days.

(21) Appl. No.: 13/835,880

(22) Filed: Mar. 15, 2013

(65) Prior Publication Data

US 2014/0278530 A1    Sep. 18, 2014

(51) Int. Cl.
*G06Q 10/00* (2012.01)
*G06F 16/58* (2019.01)
*G16H 40/67* (2018.01)
*G16H 30/20* (2018.01)

(52) U.S. Cl.
CPC ............. *G06F 16/58* (2019.01); *G16H 30/20* (2018.01); *G16H 40/67* (2018.01)

(58) Field of Classification Search
CPC .. G06F 19/321; G06F 19/322; G06F 19/3487; G06F 17/30; G06F 15/177; G06Q 50/22; G06Q 50/24; G06K 9/00
USPC ................. 705/2, 3; 707/802, 1; 706/45, 62; 358/1.15; 382/305, 128; 702/19; 709/220; 713/161
See application file for complete search history.

(56) References Cited

U.S. PATENT DOCUMENTS

| 6,912,061 B1* | 6/2005 | Ozaki ............... H04N 1/00641 358/1.15 |
| 7,028,182 B1* | 4/2006 | Killcommons ......... H04L 63/06 713/161 |
| 7,558,846 B2* | 7/2009 | Gu ...................... H04L 12/2805 709/220 |
| 7,702,600 B2* | 4/2010 | Deshpande ..................... 706/45 |
| 7,788,040 B2* | 8/2010 | Haskell et al. .................. 702/19 |

(Continued)

OTHER PUBLICATIONS

WO 2012000073 A1, Brodie et al., Publication Date: Jan. 5, 2012.*

(Continued)

*Primary Examiner* — Dilek B Cobanoglu
(74) *Attorney, Agent, or Firm* — Fish & Richardson P.C.

(57) ABSTRACT

Computer-implemented methods, computer-readable storage media, and computer systems for associating received medical imaging data with stored medical imaging data. Medical imaging data associated with a patient is received from a client device. The medical imaging data includes an image object, one or more data objects related to the image object, and metadata associated with the patient encoded in Digital Imaging and Communication in Medicine (DICOM) format. The metadata includes personal information about the patient, and time and location at which the DICOM image file was captured. The received metadata is compared with existing metadata associated with multiple existing patients to identify a subset of the existing patients who may be a potential match to the patient. Selection of an existing patient from among the subset is requested. When received, the medical imaging data is associated with the existing patient.

11 Claims, 5 Drawing Sheets

(56) References Cited

U.S. PATENT DOCUMENTS

| | | | |
|---|---|---|---|
| 7,813,594 B2* | 10/2010 | Edwards et al. | 382/305 |
| 8,140,350 B2* | 3/2012 | Rothpearl | G06F 16/58 705/2 |
| 8,442,358 B2* | 5/2013 | Rankin | G06T 9/00 382/128 |
| 8,489,410 B2* | 7/2013 | Rothpearl | G06Q 10/06 705/2 |
| 8,654,139 B2* | 2/2014 | Jakobovits | G06F 17/3028 345/581 |
| 8,799,650 B2* | 8/2014 | Duma | G16H 10/65 713/165 |
| 8,805,890 B2* | 8/2014 | Zhang et al. | 707/802 |
| 8,874,453 B2* | 10/2014 | Menschik et al. | 705/3 |
| 2002/0091659 A1* | 7/2002 | Beaulieu | G16H 30/40 706/62 |
| 2004/0061889 A1* | 4/2004 | Wood et al. | 358/1.15 |
| 2007/0067252 A1* | 3/2007 | Hengerer | G06F 19/321 |
| 2009/0103789 A1* | 4/2009 | Danner | G06F 19/321 382/128 |
| 2010/0088117 A1* | 4/2010 | Belden et al. | 705/3 |

OTHER PUBLICATIONS

Google patents search result, Jan. 5, 2015.*
Google patents search, Aug. 17, 2015.*
Google patents search, Mar. 10, 2017.*
Google patents search, Oct. 3, 2017.*
Google patents search, Sep. 5, 2019 (Year: 2019).*
Google patents search, Jun. 3, 2020 (Year: 2020).*
Ip.com search, Feb. 9, 2021 (Year: 2021).*
Zhang et al., "Web based electronic patient records for collaborative medical applications," *Computerized Medical Imaging and Graphics*, vol. 29, Issues 2-3, Mar.-Apr. 2005, pp. 115-124.
Zhang et al., "PACS and Web based image distribution and display," *Computerized Medical Imaging and Graphics*, vol. 27, Issues 2-3, Mar.-Jun. 2003, pp. 197-206.
Kim et al., "*A Web Based Medical Image Data processing and Management System*," Proceeding VIP '00 Selected Papers from the Pan-Sydney workshop on Visualisation—vol. 2, ISBN 0-909-92580-1, 2000, pp. 89-91.
Münch et al., "*A secure software architecture for collecting and processing medical image data in centers of excellence*," International Congress Series, vol. 1281, CARS 2005: Computer Assisted Radiology and Surgery, Proceedings of the 19$^{th}$ International Congress Exhibition, May 2005, p. 938-942.
CoreLab Partners, "*Medical Imaging*," Medical Imaging Assessment Technology, Internet Media Transfer, [online], <http://www.corelabpartners.com/Technology/Medical-Imaging.aspx>, site visited Feb. 27, 2013, 2 pages.

* cited by examiner

ASSOCIATING RECEIVED MEDICAL IMAGING DATA TO STORED MEDICAL IMAGING DATA

TECHNICAL FIELD

This disclosure relates to computer-implemented methods, computer-readable storage media, and computer systems for managing medical imaging data.

BACKGROUND

Patients in many health care environments are highly mobile. This particularly applies to patients seen at tertiary care centers. Often a majority of patients seen at tertiary care centers receive their primary care elsewhere. This often includes prior diagnostic imaging. Review of available prior diagnostic imaging is frequently a focal step in the care or treatment decision making process. For many diagnoses, care cannot proceed until diagnostic imaging is available for the provider to review. For these reasons, the timely availability and accessibility of outside diagnostic medical imaging can be important to providing efficient care and patient satisfaction.

SUMMARY

This disclosure relates to computer-implemented methods, computer-readable storage media, and computer systems for associating received medical imaging data to stored medical imaging data.

In general, one innovative aspect of the subject matter described here can be implemented as a computer-implemented method. Medical imaging data associated with a patient is received from a client device. The medical imaging data includes an image object, one or more data objects related to the image objects, and metadata associated with the patient. The image object and the one or more data objects can be encoded in Digital Imaging and Communication in Medicine (DICOM) format. The metadata includes, for example, personal information about the patient, and time and location at which the DICOM image file was captured. The received metadata is compared, by a computer system, with existing metadata associated with multiple existing patients. The existing metadata is stored in a database. Based on a result of the comparing, a subset of the multiple existing patients is identified as a potential match with the patient. The subset of the multiple existing patients is provided, and a selection of an existing patient from among the subset is requested. Input selecting an existing patient is received. The medical imaging data including the image object, one or more data objects related to the image object and the metadata are provided to be associated with the existing patient.

This, and other aspects, can include one or more of the following features. Based on the result of the comparing, it can be determined that no existing patient in the database is a potential match with the patient. In response, a new patient record can be generated using a HL7 ADT A04 patient registration message or electronic health record system specific web services call. The medical imaging data including the image object, one or more data objects related to the image object and the metadata associated with the patient can be provided to be associated with the new patient record. The received metadata can include a first name, a last name, a sex, and a date of birth of the patient. Based on the result of the comparing, it can be determined that a first name, a last name, a sex, and a date of birth of an existing patient in the database matches the first name, the last name, the sex, and the date of birth, respectively, of the patient. In response, the medical imaging data including the image object, one or more data objects related to the image object and the metadata can be provided to be associated with the existing patient by generating either an HL7 ADT A24 link patient information message or an HL7 ADT A40 merge patient message.

The database can store multiple Electronic Health Records. Comparing the received metadata with the existing metadata can include querying the PACS with a DICOM C-FIND procedure. Receiving the medical imaging data from the client device can include receiving the medical imaging data by executing a computer software application remotely from the client device without installing the computer software application on the client device. The medical imaging data can be stored on a computer-readable storage medium connected to the client device. Executing the computer software application remotely from the client device can include executing the application to search the computer-readable storage medium for medical imaging data, and identifying the medical imaging data in response to searching the computer-readable storage medium.

The client device can be connected to a local network accessible to local medical imaging systems configured to acquire or store DICOM data. Executing the computer software application remotely from the client device can include presenting an Internet Protocol (IP) address of the medical imaging system, a listening Transmission Control Protocol (TCP) port, and a DICOM Application Entity (AE) title in a display device connected to the medical imaging system,. A connection to the medical imaging system can be formed using the IP address, the TCP port, and the DICOM AE title. The received medical imaging data can be provided through the connection. It can be determined that a user of the client device is an authenticated provider of medical imaging data. The medical imaging data including the image object, the one or more data object related to the image objects, and the metadata associated with the patient can be provided without verifying that the received data is medical imaging data. It can be determined that a user of the client device is not an authenticated provider of medical imaging data. In response, a hold can be placed on the providing of the medical imaging data until the received data has been verified as medical imaging data. The client device can be requested to provide information describing the received data and a reason for providing the received data. The information can be received from the client device. The received data can be verified as medical imaging data automatically and without user intervention based on the information. The information and at least a portion of the received data can be displayed in a display device. Confirmation that the received data is medical imaging data can be requested.

A request for an imaging study overread can be received from the client device. It can be determined that the patient is an existing patient. Upon determining that the patient is an existing patient, the medical imaging data can be automatically linked to the existing patient in response to receiving the request for the imaging study overread. It can be determined that the patient is a new patient. Upon determining that the patient is a new patient, a new patient record can be generated for the patient, and the medical imaging data can be automatically linked to the new patient in response to receiving the request for the imaging study overread.

Another innovative aspect of the subject matter described here can be implemented as a computer-readable medium storing instructions executable by data processing apparatus to perform operations described here. A further innovative aspect of the subject matter described here can be implemented as a system that includes the computer-readable medium storing the instructions and the data processing apparatus to execute the stored instructions.

While generally described as computer-implemented software embodied on tangible media that processes and transforms the respective data, some or all of the aspects may be computer-implemented methods or further included in respective systems or other devices for performing this described functionality. The details of these and other aspects and implementations of the present disclosure are set forth in the accompanying drawings and the description below. Other features and advantages of the disclosure will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
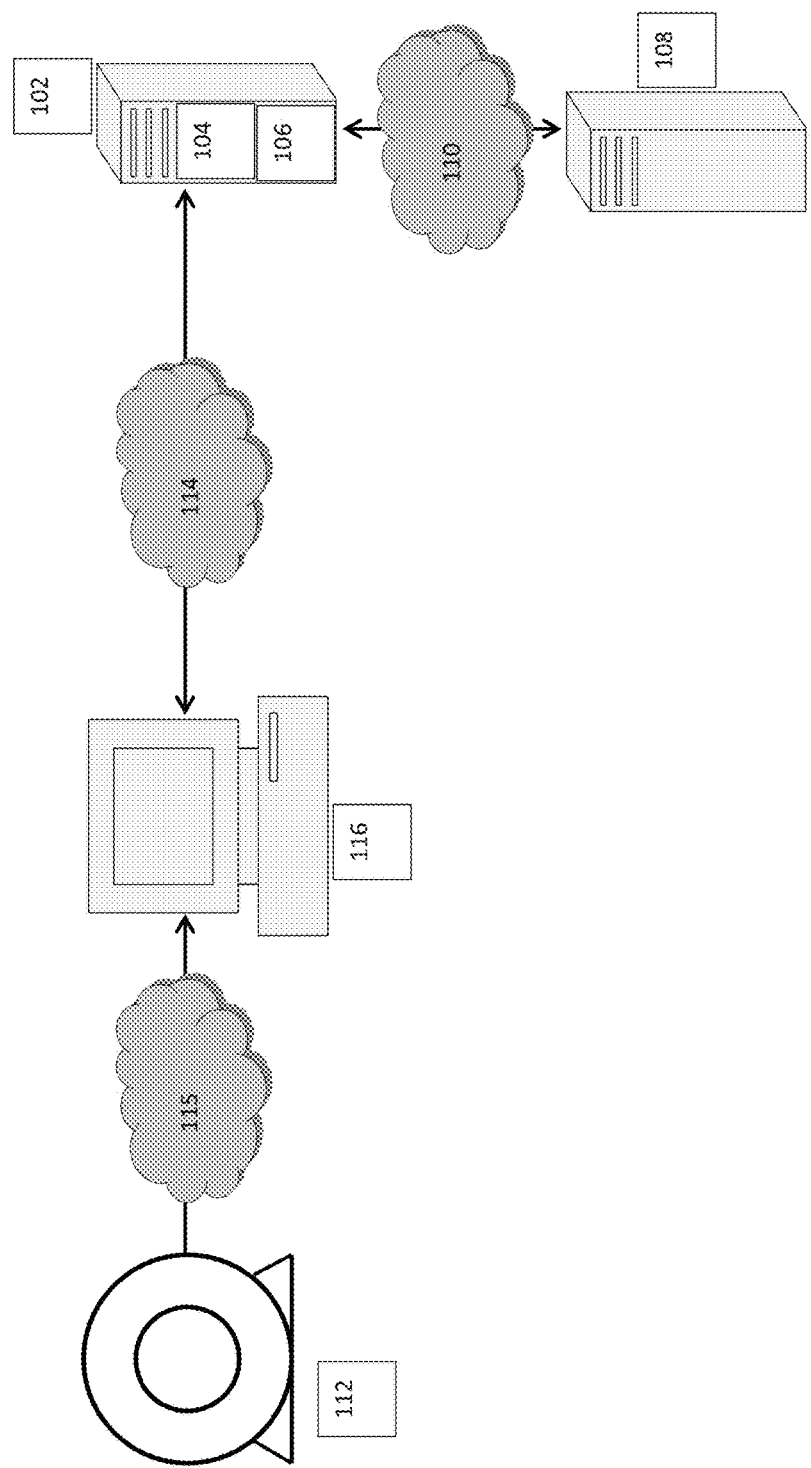
FIG. 1 illustrates an example computer system for associating received medical imaging data with stored medical imaging data.

This disclosure relates to computer-implemented methods, computer-readable storage media, and computer systems for associating received medical imaging data to stored medical imaging data. One method for transport of prior medical imaging data is on physical media (CD, DVD, flash memory, such as thumb drive or flash memory card, or other similar physical media). Outpatients who have been referred from outside for tertiary care will frequently bring physical media with prior imaging to their initial office appointment. Perhaps more frequently, outside imaging has to be requested and sent by courier after the initial office visit. In both cases, review of the imaging is often delayed precluding moving forward with care decisions. Review of medical imaging directly from physical media can be slow and tedious for providers, particularly when the medical imaging viewer software to view the medical imaging data included on the physical media is unfamiliar to the provider or limited in the features offered (or both). Because of the limitations of viewing outside medical imaging directly from physical media, most providers prefer to have outside patient medical imaging loaded onto the enterprise medical imaging archive and review system or PACS (picture archiving and communication system). This allows outside imaging to be viewed across the health care enterprise with a system with which the providers are quite familiar and adept. Loading outside medical imaging data onto the PACS also allows the medical imaging data to be compared directly to any other medical imaging data within the archive.

For the above reasons, medical imaging received on physical media is routinely sent by clinical providers to be loaded onto the PACS. However, certain limitations of physical media can result in resources (for example, personnel resources) being expended and delays being introduced to patient care. Such limitations can include a need to take physical media to a few dedicated workstations to be loaded to the PACS or to send the physical media via interoffice mail to the radiology file room. In some environments, a large quantity of physical media (for example, in excess of 800 CDs and DVDs) are encountered each week. In such environments, this quantity can represent a relatively small fraction of all outside imaging brought in by patients for review by their providers.

A technique that can be implemented to decrease the volume of outside medical imaging data transported on physical media can include building persistent dedicated VPN connections between regional institutions. Institutions can then send medical imaging studies on demand without the need to use physical media. However, dedicated site-to-site VPN's can incur significant costs such as personnel to setup and maintain the connections and the need for dedicated VPN hardware at each end of a VPN connection.

Facilitating the transfer and importation of medical imaging data alone does not address other segments of the outside imaging workflow including order generation and linking or matching with other existing medical records or medical imaging. Providers often desire internal interpretations (overread) of submitted outside medical imaging. This facilitates comparison to any existing internal imaging that may exist. Outside interpretations may also not be available with submitted outside imaging. Requests for outside imaging overreads are submitted independently from submission of the imaging itself. This leads to additional manual workflows requiring personnel to manually match submitted imaging with orders for imaging overreads.

This disclosure describes techniques to transport medical imaging data from physical media or other sources (for example, medical imaging modalities; a modality can be any device which acquires or generates medical imaging, e.g. CT scanner, MRI scanner, x-ray image processor, ultrasound machine, image processing workstation, etc.) at the point of care or remotely onto a central server or PACS. In addition, this disclosure describes techniques to evaluate the received data within a rules engine and to automate medical imaging data workflow tasks for outside imaging that previously would have been performed manually in multiple separate systems. The techniques can be implemented as a clientless (i.e., without requiring installation of a local application) web accessible computer software application that can be launched on a remote client device. The computer software application can offer two distinct functional modes of operation for transporting medical imaging.

The first functional mode can be implemented to enable providers to transfer medical image data from physical media or locally or network accessible storage to a database, such as PACS, over a network. Providers can be, for example, internal providers or remote external providers (or both). As described below with reference to the following figures, a computer system for managing the medical imaging data can authenticate a user who wants to provide medical imaging data associated with a patient, and can collect additional metadata about the user or the patient (or both). The computer system can then launch the computer software application. The computer system can implement the application to request the user to select a local directory or drive that contains the medical imaging data or the physical media. The computer system can execute the application to scan the directory tree or physical media and to identify one or more or all medical imaging files, specifically files conforming to the DICOM (Digital Imaging and Communications in Medicine) standard. The computer system can execute the application to transfer one or more or all identified DICOM files over an encrypted connection to a server computer system. The computer system can either directly forward the files into the PACS or hold the files for verification by file room personnel prior to transfer to PACS.

The second functional mode can be implemented to enable medical imaging data to be transferred directly from a medical imaging device (modality) over one or more wired or wireless networks as an alternative to or in addition to enabling transfer from a directory or physical media. In this mode, the computer system can detect that a user, for example, at a remote health organization has accessed a webpage of a website hosted by the computer system. The computer system can allow for authentication and collection of metadata through the webpage. Upon launching of the web application, a client device can function as a medical imaging receiver (specifically a DICOM storage SCP). A local modality can then send imaging directly to the computer system that executes a computer software application to transfer the imaging via an encrypted session to a server in a similar manner to the first functional mode. Effectively this mode creates an ad hoc VPN connection for transferring medical imaging from one location directly to another location implementing the computer system. A connection can be created on demand, and no dedicated hardware is required.

FIG. 1 illustrates an example computer system 102 for associating received medical imaging data with stored medical imaging data. The computer system 102 can implement the techniques described here for managing medical imaging data as computer instructions stored on a computer-readable medium 104 and executed by data processing apparatus 106. For example, the computer system 102 can be a server, desktop computer system, a laptop computer system, a tablet computer system, a smartphone, a personal digital assistant (PDA), or any other suitable computer system. In some implementations, the computer system 102 can be connected to one or more servers represented by computer system 108 (for example, directory services server, EHR server, PACS server) over one or more wired or wireless networks 110 (for example, local enterprise network or the Internet). The computer system 102 can be connected to a client device 116 over one or more wired or wireless networks 114. A modality 112 can be connected to client device 116 over one or more wired or wireless networks 115. Networks 114 and networks 115 may or may not be the same physical network in whole or in part. As described below with reference to FIGS. 2 and 3, the computer system 102 can implement workflows to receive medical imaging data from the modality 112 via networks 115 through client device 116 or directly from the client device 116 (or both) over the networks 114, implement rules to analyze the received medical imaging data, and to provide the medical imaging data to the server computer system 108 over the networks 110, for example, to be associated with a patient having information stored on the server computer system 108. In some implementations, the computer system 102 can be a stand-alone computer system while, in other implementations, the computer system 102 can be a component of and be included in the server computer system 108 or operate in conjunction with one or more servers represented by computer system 108.

Figure 2:
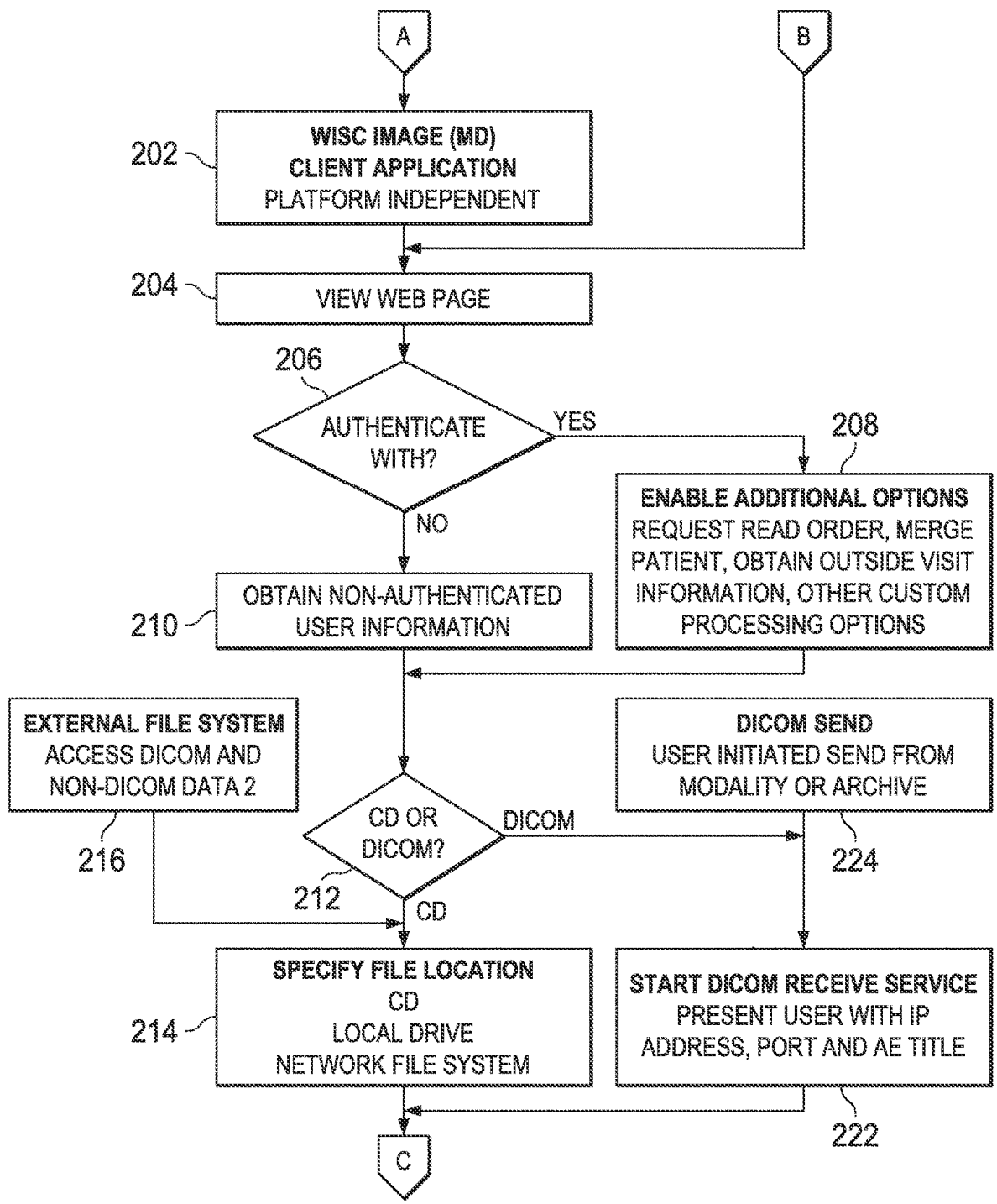
FIG. 2 describes an example workflow implemented by a client device for providing medical imaging data from local media, network accessible storage, or via DICOM protocol network transfer to the server computer system.
Figure 2:
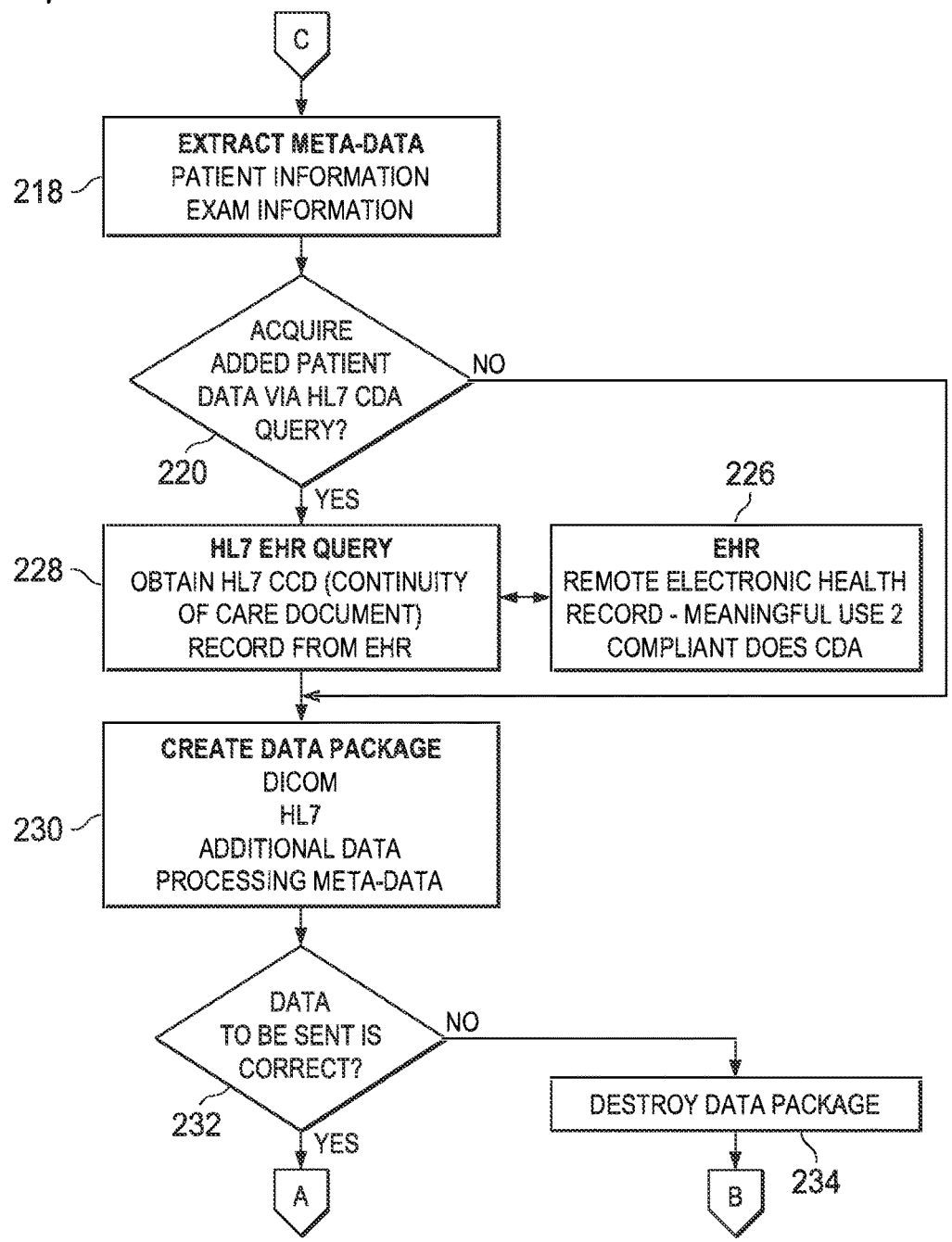

FIG. 2 describes an example workflow implemented by a client device 116 and optionally a modality 112 for providing medical imaging data to the computer system 102. A "user" and a "client device," as used in this disclosure, can represent a computer system or a person using a computer system. For example, either "user" or "client device" or both can be a person using a computer system. Alternatively, either "user" or "client device" or both can be the computer system itself. A computer system can be a server, desktop computer system, a laptop computer system, a tablet computer system, a smartphone, a personal digital assistant (PDA), or any other suitable computer system.

In some implementations, the client device can initiate a session to provide medical imaging data. For example, the client device can open a bi-directional HTTPS encrypted connection to access the computer system 102 that hosts a computer software application that the client device will execute to provide the medical imaging data. To do so, a user of the client device 116 can provide a URL (Uniform Resource Locator) referencing a web page of a website hosted by the computer system 102 in a user interface (for example, an Internet browser). In response, the computer system 102 can provide the computer software application to the client device 116. The computer software application can be a platform independent application 202. That is, the necessary software components needed on the client device 116 can be dynamically downloaded and executed without needing to be persistently installed or persistently stored locally on the client device 116.

At 204, the client device 116 can display the web page, for example, in a display device. As an initial step, the computer system 102 can authenticate the client device 116, for example, to determine if the client device 102 is authorized to provide medical imaging data using the computer software application. In some implementations, the computer system 102 can execute the computer software application to authenticate users or enable users to proceed without authentication to an internal authority.

Authentication can be utilized by users internal to the enterprise. As external users may not have an enterprise account to authenticate against, the computer system 102 can allow collection of non-authenticated user information. In some implementations, the computer system 102 can differentiate internal and external users based, at least in part, on the client IP address. At 206, the computer system 102 can authenticate users using, for example, metadata found in an LDAP or Active Directory service within the enterprise. If the computer system 102 can authenticate the user (decision branch "Yes"), then, at 208, the computer system 102 can present the client device 116 with additional data entry options such as the ability to directly initiate and request overreads, merge outside imaging to an existing internal patient record, obtain outside visit information, or a variety of other custom processing options. If the computer system 102 cannot authenticate the user (decision branch "No"), then, at 210, the computer system 102 can prompt the unauthenticated user for contact information and the reason for submission of medical imaging.

After authentication and metadata collection, at 212, the client device 116 can determine whether the medical imaging data to be transferred to computer system 102 is located within a file system accessible to client device 116 (e.g. local directory, local drive, or mapped network share) or will be sent from modality 112 over networks 115 through client device 116 to computer device 102. In some implementations, the computer system 102 can display one or more messages (for example, prompts) which the user can to select to communicate whether the medical imaging data will be submitted from files or via direct DICOM network transfer.

If client device 116 (decision branch "CD"), then the application provided for execution computer system 102 to client device 116 can search one or more computer-readable storage media associated with (for example, connected to) the client device 116 for medical imaging data. To do so, in some implementations, the application provided by computer system 102 can access the local file system of the client device 116 to obtain for medical imaging from physical media, a local directory, or from a network file system. In some implementations, at 216, the computer system 102 can access external file systems to search for and obtain DICOM and non-DICOM data.

For example, the computer system 102 can load a Java applet within the client device 116's browser in order to access the client device's local file system. Local file system access from within a browser session can be supported via a number of methods within the HTML5 standard including the "File API"; however, support for HTML5 API's is not universal across browsers. As modern browsers that support this functionality and support calling Java classes directly from Javascript are adopted, Java applet loading will no longer be required.

When the user specifies file based data submission, the computer system 102 can execute the computer software application to present a directory selection dialog box. The user may pick any accessible file systems including a local physical media CT or DVD drive, a directory on a local hard drive, or a directory on a network file system. Upon selection of a file system location, the applet initiates a search from the root of the selected file system directory and identifies medical imaging data files (DICOM) as well as potentially related data files (.JPG, .TIF, .DOC, .TXT, .XML, and .PDF files). Data transfer can be initiated to the computer system 102 in the background. Ongoing transfer status is updated for the user based on the number of files transferred relative to the number of files located.

If modality 112 will be used to send medical imaging (decision branch "DICOM"), then the computer system 102 can load a Java applet within the client device 116 browser. When executed, the Java applet starts a DICOM receive service (specifically DICOM Storage SCP). The user is presented with the client device 116's IP address, listening TCP port, and the DICOM Application Entity (AE) title. Similar to the case of file based submission, as modern browsers that support calling of Java classes directly from within HTML5 Javascript, the need to run a Java applet will be mitigated. At 224, after configuring DICOM network destination using the IP address, TCP port, and AE title for client device 116, the user can initiate a DICOM send from the modality 112 or an archive connected to the modality 112 (or both) to send the medical imaging data to client device 116. At 222, the client device 116 can start receiving the medical imaging data. Transfer of received DICOM objects is initiated immediately in the background to computer device 102. In this manner, the computer system 102 can receive medical imaging data that is either stored on a physical media (such as CD or DVD) or file systems accessible to client device 116 or from a modality 112 that can access client device 116 over networks 115.

When the user specifies DICOM network transfer for importing data, the computer system 102 can initialize a Java applet on client device 116. The computer system 116 can then start a DICOM storage SCP (Service Class Provider) listener. The IP address of client device 116 running the applet, the listening TCP port number, and the configured DICOM AE (Application Entity) title are displayed for the user. In order to receive DICOM data, the user can initiate a DICOM transfer from modality 112. Modality 112 can be any device (e.g. imaging modalities, DICOM archives including most PACS systems, image processing workstations, etc.) that supports sending DICOM data via the DICOM application layer protocol (specifically, the device must support the DICOM storage SCU role). Transfer of received objects to the computer system 102 server is initiated immediately in the background as data is received by client device 116.

During receipt of DICOM data, at 218, the client device 116 can extract metadata including patient information, exam information, and other suitable information. In some implementations, the client device 116 can extract metadata from DICOM data during the scanning phase in the case of file-based data submission or during receipt of DICOM data in the case of network-based DICOM data. In some implementations, extraction of metadata is performed on computer system 102. Metadata extracted from identified DICOM medical imaging files may include items such as patient name (DICOM tag 0010,0010), patient medical record number (DICOM tag 0010,0020), patient birthdate (DICOM tag 0010,0030), patient sex (DICOM tag (0010, 0040), modality (DICOM tag 0008,0060), study description (DICOM tag 0008,1030), institution name (DICOM tag 0008,0080), study date (DICOM tag 0008,0020), study time (DICOM tag 0008,0030), and referring physicians name (DICOM tag 0008,0090). If extracted on client device 116, the extracted metadata is communicated to the computer system 102.

At 220, the computer system 102 can determine whether added patient data is to be acquired via HL7 Clinical Document Architecture (CDA). If yes (decision branch "Yes"), then, at 228, the client device 116 can obtain HL7 Continuity of Care Document (CCD) record from the EHR. The HL7 Clinical Document Architecture (CDA) standard provides for interchange of clinical medical documents. The HL7 CDA is mandated by Meaningful Use 2 to enable exchange of health care data including imaging reports. The Continuity of Care Document (CCD) is a specific CDA patient summary document for interorganizational exchange. Metadata extraction from imaging reports or CCD's available as XML files can be supported. At 226, standard HL7 messaging semantics can be supported by including HL7 functionality into the applet running on client device 116 to allow for query and receipt of HL7 CDA reports and CCD's based utilizing patient and exam identifiers extracted from DICOM (patient ID, date of birth, accession number, etc.).

If no (decision branch "NO"), then, at 230, the computer system 102 can create a data package and verify user data. The computer system 102 can format the metadata extracted from the identified files or network received objects and display the metadata on client device 116 for the user. This provides an opportunity for the user to view a list of medical imaging studies present within the identified files or via network transfer. All data being transferred (whether identified from files or received via network transfer) and all associated metadata is treated as a data package. If an authenticated user indicated that overreads were being requested, the specific exam(s) (if multiple exams were found) to be interpreted can be indicated by the user. The user on client device 116 has the option to finalize the submission.

At 232, it can be checked whether the data to be sent is correct. If the data to be sent is correct (decision branch "Yes"), then the medical imaging data and the metadata are released for subsequent processing on computer system 102. In some implementations, user verification may occur asynchronously with ongoing data transfer. When the user finalizes the submission, the data package is released for subsequent steps on computer system 102. If data to be sent is not correct (decision branch "No"), then the client device 116 user cancels submission, and the data package is destroyed. Any ongoing data transfer if present is cancelled. Limited metadata may be kept on the computer system 102 to facilitate support and troubleshooting, but all data files are deleted.

Figure 3:
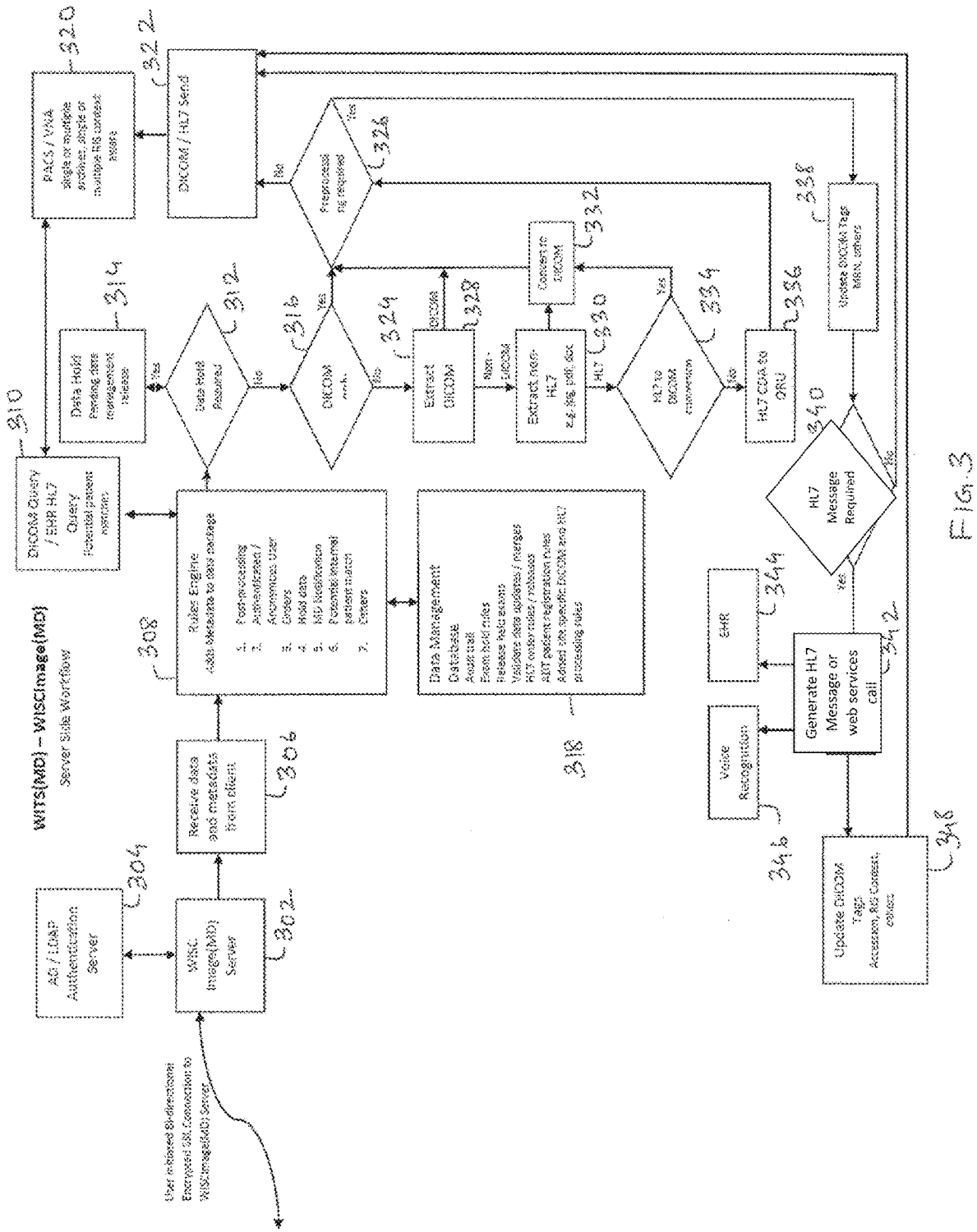
FIG. 3 describes an example workflow implemented by a server computer system for receiving and processing medical imaging data.

FIG. 3 describes an example workflow of additional processing implemented by computer system 102 for receiving and processing medical imaging data. At 302, the computer system 102 receives data and metadata from client device 116. Credentials passed from client device 116 described above in paragraph 0022 are used to authenticate the client device 116 user with server computer system 108. To do so, at 304, a call is made via LDAP (Lightweight Directory Access Protocol) or other authentication protocol to authenticate the user against an enterprise authority. The enterprise authority can be Microsoft Active Directory based or another directory services that utilizes LDAP for authentication requests. When a user is authenticated against a directory, additional information about the user can be obtained from the directory service about the user including group membership status, department, role, and job title. Users who have the authority to place medical imaging orders can be identified in this way. This allows the web application to tailor the options presented to the user based on the credentials the user supplied.

At 306, the server computer system 102 can receive medical imaging data and metadata from the client device 116 or the modality 112. In this step the data package contents are prepared for rules engine evaluation. Metadata entered by the remote client device is mapped to appropriate variables for the subsequent evaluation. Binary DICOM files are internally converted to an XML representation to facilitate processing in the rules engine. An example of a DICOM image file in this XML format is provided below (binary pixel data is not shown):

```
<?xml version="1.0" encoding="UTF-8" standalone="no"?>
<dicom>
    <tag00020000 len="4" tag="00020000" vr="UL">182</tag00020000>
    <tag00020001 len="2" tag="00020001" vr="OB">00\01</tag00020001>
    <tag00020002 len="26" tag="00020002" vr="UI">1.2.840.10008.5.1.4.1.1.2</tag00020002>
    <tag00020003 len="54" tag="00020003"
        vr="UI">1.2.840.113619.2.55.3.1753275364.5848.1173415047.614.3</tag00020003>
    <tag00020010 len="18" tag="00020010" vr="UI">1.2.840.10008.1.2</tag00020010>
    <tag00020012 len="16" tag="00020012" vr="UI">1.2.40.0.13.1.1</tag00020012>
    <tag00020013 len="14" tag="00020013" vr="SH">dcm4che-1.4.27</tag00020013>
    <tag00080005 len="10" tag="00080005" vr="CS">ISO_IR 100</tag00080005>
    <tag00080016 len="26" tag="00080016" vr="UI">1.2.840.10008.5.1.4.1.1.2</tag00080016>
    <tag00080018 len="54" tag="00080018"
        vr="UI">1.2.840.113619.2.55.3.1753275364.5848.1173415047.614.3</tag00080018>
    <tag00080020 len="8" tag="00080020" vr="DA">20070309</tag00080020>
    <tag00080030 len="14" tag="00080030" vr="TM">150539.000000</tag00080030>
    <tag00080050 len="0" tag="00080050" vr="SH"/>
    <tag00080060 len="2" tag="00080060" vr="CS">CT</tag00080060>
    <tag00080090 len="2" tag="00080090" vr="PN"/>
    <tag0008103E len="20" tag="0008103E" vr="LO">Smart Score 0.35 sec</tag0008103E>
    <tag00100010 len="10" tag="00100010" vr="PN">Anonymous</tag00100010>
    <tag00100020 len="8" tag="00100020" vr="LO">1717319</tag00100020>
    <tag00100030 len="8" tag="00100030" vr="DA">19490505</tag00100030>
    <tag00100040 len="2" tag="00100040" vr="CS">M</tag00100040>
    <tag00101010 len="4" tag="00101010" vr="AS">057Y</tag00101010>
    <tag00180022 len="10" tag="00180022" vr="CS">CINE MODE</tag00180022>
    <tag00180050 len="8" tag="00180050" vr="DS">2.500000</tag00180050>
    <tag00180060 len="4" tag="00180060" vr="DS">120</tag00180060>
    <tag00180090 len="10" tag="00180090" vr="DS">500.000000</tag00180090>
    <tag00181020 len="8" tag="00181020" vr="LO">06MW29.7</tag00181020>
    <tag00181030 len="62" tag="00181030" vr="LO">5.14 SnapShot Segment 0.625 mm 30-75 BPM
        – LARGE + smart score</tag00181030>
    <tag00181100 len="10" tag="00181100" vr="DS">250.000000</tag00181100>
    <tag00181110 len="10" tag="00181110" vr="DS">949.075012</tag00181110>
    <tag00181111 len="10" tag="00181111" vr="DS">541.000000</tag00181111>
    <tag00181120 len="8" tag="00181120" vr="DS">0.000000</tag00181120>
    <tag00181130 len="10" tag="00181130" vr="DS">161.209000</tag00181130>
    <tag00181140 len="2" tag="00181140" vr="CS">CW</tag00181140>
    <tag00181150 len="4" tag="00181150" vr="IS">227</tag00181150>
    <tag00181151 len="4" tag="00181151" vr="IS">400</tag00181151>
    <tag00181152 len="2" tag="00181152" vr="IS">11</tag00181152>
    <tag00181160 len="12" tag="00181160" vr="SH">BODY FILTER</tag00181160>
    <tag00181170 len="6" tag="00181170" vr="IS">48000</tag00181170>
    <tag00181190 len="8" tag="00181190" vr="DS">1.200000</tag00181190>
    <tag00181210 len="8" tag="00181210" vr="SH">STANDARD</tag00181210>
    <tag00185100 len="4" tag="00185100" vr="CS">FFS</tag00185100>
    <tag0020000D len="52" tag="0020000D"
        vr="UI">1.2.840.113619.2.55.3.1753275364.5848.1173415047.607</tag0020000D>
    <tag0020000E len="52" tag="0020000E"
        vr="UI">1.2.840.113619.2.55.3.1753275364.5848.1173415047.613</tag0020000E>
```

-continued

```
<tag00200010 len="6" tag="00200010" vr="SH">10651</tag00200010>
<tag00200011 len="2" tag="00200011" vr="IS">2</tag00200011>
<tag00200012 len="2" tag="00200012" vr="IS">1</tag00200012>
<tag00200013 len="2" tag="00200013" vr="IS">3</tag00200013>
<tag00200032 len="34" tag="00200032" vr="DS">-88.300003\-125.000000\-
    66.750000</tag00200032>
<tag00200037 len="54" tag="00200037"
    vr="DS">1.000000\0.000000\0.000000\0.000000\1.000000\0.000000</tag00200037>
<tag00200052 len="62" tag="00200052"
    vr="UI">1.2.840.113619.2.55.3.1753275364.5848.1173415047.608.21129.0.1</tag00200052>
<tag00201040 len="2" tag="00201040" vr="LO">SN</tag00201040>
<tag00201041 len="10" tag="00201041" vr="DS">-66.750000</tag00201041>
<tag00280002 len="2" tag="00280002" vr="US">1</tag00280002>
<tag00280004 len="12" tag="00280004" vr="CS">MONOCHROME2</tag00280004>
<tag00280010 len="2" tag="00280010" vr="US">512</tag00280010>
<tag00280011 len="2" tag="00280011" vr="US">512</tag00280011>
<tag00280030 len="18" tag="00280030" vr="DS">0.488281\0.488281</tag00280030>
<tag00280100 len="2" tag="00280100" vr="US">16</tag00280100>
<tag00280101 len="2" tag="00280101" vr="US">16</tag00280101>
<tag00280102 len="2" tag="00280102" vr="US">15</tag00280102>
<tag00280103 len="2" tag="00280103" vr="US">1</tag00280103>
<tag00280120 len="2" tag="00280120" vr="US">63536</tag00280120>
<tag00281050 len="2" tag="00281050" vr="DS">40</tag00281050>
<tag00281051 len="4" tag="00281051" vr="DS">400</tag00281051>
<tag00281052 len="6" tag="00281052" vr="DS">-1024</tag00281052>
<tag00281053 len="2" tag="00281053" vr="DS">1</tag00281053>
<tag00281054 len="2" tag="00281054" vr="LO">HU</tag00281054>
<tag00282110 len="2" tag="00282110" vr="CS">00</tag00282110>
</dicom>
```

At 308, a rules engine can add metadata to the data package. The computer system 102 can implement the rules engine as a computer software application including computer instructions stored on a computer-readable medium and executable by data processing apparatus. The computer system 102 can process the received data and metadata to automate manual procedure steps and perform functions not available elsewhere within a single application. The tasks performed by the rules engine application fall into several broad categories including: dataset verification, patient identification, data and metadata conversion to consumable health care data formats (for example, DICOM and HL7), notification, auditing, and order generation.

At 312, the computer system 102 can execute the rules engine to determine if data hold is required. If data hold is required (decision branch "Yes"), then, at 314, the computer system 102 can hold submitted data sets for verification. In some implementations, the computer system 102 can hold the submitted datasets for verification prior to sending the datasets to downstream systems based on configurable preferences. Datasets submitted by internal authenticated users would generally be considered trusted and configured to be processed immediately. Conversely, datasets submitted by non-authenticated users from outside the institution would generally be held prior to being released to downstream systems (e.g. prior to uploading DICOM objects to PACS). If no dataset hold is required by the configured rules (decision branch "No"), then the dataset is released for downstream processing and subsequently to downstream systems.

At 316, the computer system 102 can determine if the medical imaging data and metadata received from the client device 116 or the modality 112 includes DICOM data only. If the computer system 102 determines that the medical imaging data includes DICOM data only (decision branch "Yes"), then, at 326, the computer system 102 can determine if preprocessing is required. If the computer system 102 determines that the medical imaging data and metadata include more than DICOM data alone, then, at 324, the computer system 102 can extract and forward the DICOM data to determining if pre-processing is required. At 330, the computer system 102 can extract the non-DICOM data (for example, data in a .JPG, .PDF, .DOC format, or other non-DICOM formats). At 334, the computer system 102 can determine if the extracted data needs to be converted into DICOM format. If yes, then, at 332, the computer system 102 can convert the data into DICOM format. If no, then, at 336, the computer system 102 can forward the HL7 data to determine whether the data needs to be pre-processed.

A number of factors at 326 determine whether pre-processing of the received data is needed prior to forwarding data on to downstream systems. Additional pre-processing steps are required if the received data must be modified to conform to an existing patient record or to match an imaging order (as in the case of a requested overread). Pre-processing includes modification of any DICOM tags at 338 and 348 and any messaging to downstream systems (for example PACS, EHR, or voice recognition dictation systems) at 340 and 342 to ensure that the received data will be correctly like to the patient's record.

Outside imaging is often submitted for patients who have already been registered within the local EHR and may also have local medical imaging available within PACS or a VNA. Imaging submitted from outside institutions will include patient identifiers (e.g. MRN) from the institution where the imaging was acquired. Matching outside imaging to existing patients is nearly always a manual process. With manual work flows, personnel must manually identify potential patient matches and then manually link outside imaging to an existing patient record or manually merge a patient record containing outside imaging to an internal record. If a matching internal patient record is not present, personnel must manually perform steps to register that patient in the local EHR so that an order can be generated for an outside imaging study interpretation.

The computer system 102 can implement the computer software application to assist with automating this process by querying internal data stores to find potential patient matches. At 310 the computer system 102 can query EHR's with an HL7 ADR A19 patient query message or via vendor specific web services. Most PACS or VNA's can be queried with a DICOM C-FIND procedure. The computer system 102 can present patients with multiple matching identifiers for verification, or if sufficient patient identifier matches are present, the computer system 102 can definitively match outside imaging to an existing local patient record. For example, a patient may be considered an exact match if the patient first name, last name, middle initial, sex, and date of birth match.

If no potentially matching internal patient records are identified, patient registration would be required as a pre-processing step at 326. To accomplish this, at 342 the computer system 102 can generate a patient registration event message (HL7 ADT A04 patient registration message or web services registration event) to the EHR. An example HL7 ADT A04 message is shown below:

```
MSH|^~\&|RIS|WB0|MITRAB||201003010102||ADT^A04|45804|P|2.3.1|
EVN|A04|201003010102||||201003010102|
PID|||9999999|^^^^|LASTNAME^FIRSTNAME^MI^^||19810508|F||U|ROAD1^^MADISON^WI^88888^USA||
    6085559999|||U||||
PV1||O|OUTPATIENT
    CLINIC||||^^^^^|^^^|^^^|OUT|||||||000000^^^^^||80945768||||||||||||||||||WB0||
    ||||||||||V|
AL1|1|Dr|^SULFA DRUGS|To|HIVES/ITCHIN|20091203|
```

If instead a patient match is identified, the computer system 102 can automatically link the patient to an existing patient record by generating at 342 either an HL7 ADT A24 link patient information message or an HL7 ADT A40 merge patient message.

Within existing manual workflows, outside image dataset submission and order placement for an overread are decoupled. Order requests are placed within the EHR and outside imaging studies are uploaded to PACS or a VNA. Both of these steps must be initiated independently by the provider submitting images. A person (generally within the institution's medical imaging file room) must manually find the outside imaging study within the PACS and both link the dataset to the order and link or merge the dataset to an internal patient record.

The computer system 102 can execute the computer software application to automate the process described above as a pre-processing step determined at 326. In some implementations, if an outside imaging study overread is requested at the time of client device authentication, the computer system 102 can prompt the authenticated user to input an existing internal medical record number for the patient or confirm that the patient needs to be registered. The computer system 102 can then either automatically link the submitted imaging study to an existing patient or register the patient by implementing the techniques described above. In both cases, the computer system 102 can update the appropriate DICOM tags. To do so, the computer system 102 can generate an HL7 ORM O01 order message at 342 and send the generated message to the appropriate downstream systems which may include the EHR, PACS, and a voice recognition dictation system. An example HL7 ORM O01 message is shown below:

```
MSH|^~\&|RIS|WB0|MITRAB||201003010102||ORM^O01|45817|P|2.3.1|
EVN|O01|201003010102||||201003010102|
PID|||9999999|^^^^|LASTNAME^FIRSTNAME^MI^^||19810508|F||U|ROAD1^^MADISON^WI^88888^USA||
    6085559999|||U||||
PV1||O|OUTPATIENT
    CLINIC||||^^^^^|^^^|^^^|OUT|||||||000000^^^^^||80945768||||||||||||||||||WB0||
    ||||||||||V|
AL1|1|Dr|^SULFA DRUGS|To|HIVES/ITCHIN|20091203|
ORC|NW|58857980^001|11111|O90027|NW||1^once^^201003010102^^R^^ROUTINE|||SECLAR||000000^^^
    ^^^||||^|
```

-continued

```
OBR|58857980^001|11111|72132^CT HEAD^CPT|||||SECLAR|||||72132^CT
    HEAD^^^|000000^^^^^||11111|^CT|11111||||CT||
    ||^once^^201003010102^^R^^ROUTINE||||||||
ZDS|1.2.840.113696.827006.500.8952.20100105135829^SMS^Application^DICOM|
ZOR|1||LUMBAGO|||testing purposes||||||||||||/|EAST CLINIC SPINE NEUROSURG|
```

The order fields are populated from several combined sources. Patient identifiers (e.g. MRN) are taken from the results of queries to the EHR or PACS (in the case of existing matching patient records) or after registering the patient after sending an HL7 ADT A04 patient registration message. Most required HL7 ORM O01 fields are taken directly from the collected metadata and the metadata extracted from the submitted DICOM objects. Any required unique identifiers such as accession numbers are automatically generated.

Once all required pre-processing has occurred or if the computer system 102 determines that pre-processing is not required (decision branch "No"), then, at 322, the computer system 102 can send the DICOM data to PACS/VNA.

Figure 4:
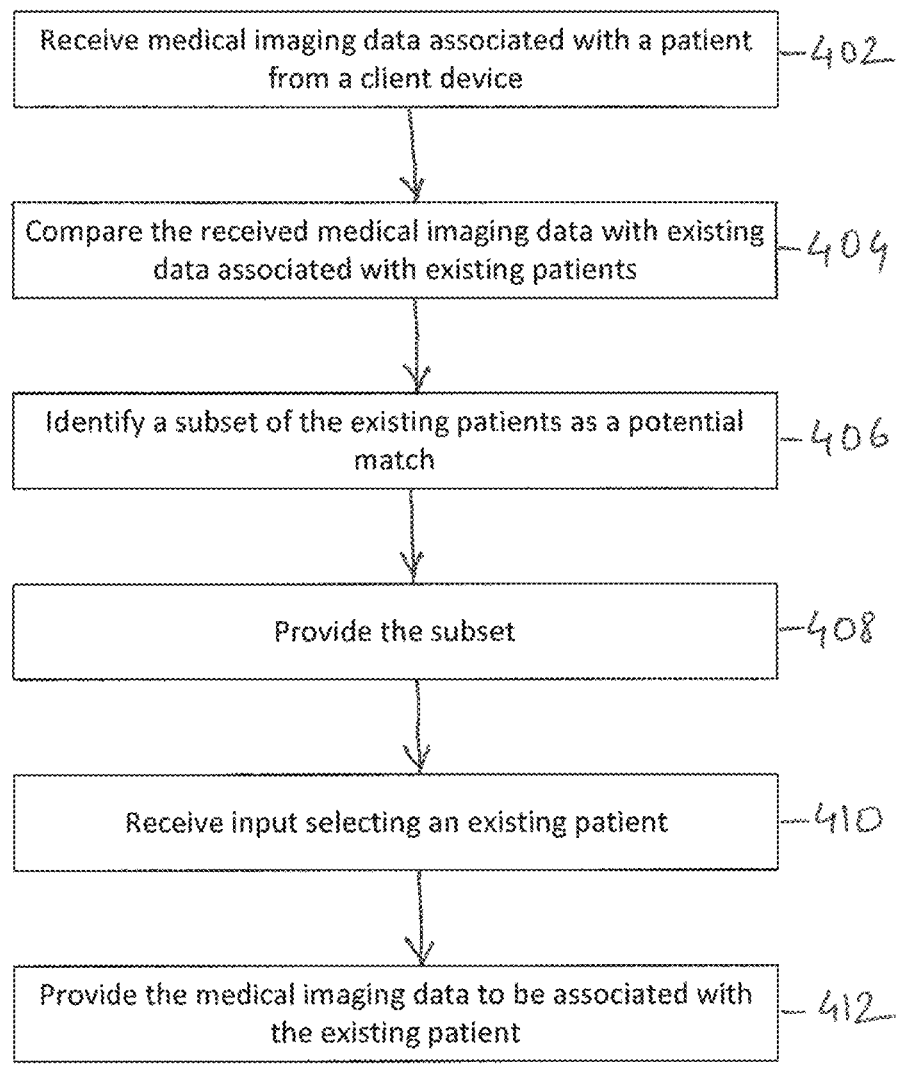
FIG. 4 is a flowchart of an example process for associating received medical imaging data to stored medical imaging data.

FIG. 4 is a flowchart of an example process 400 for associating received medical imaging data to stored medical imaging data. The process 400 can be implemented as computer instructions stored on a computer-readable medium and executable by data processing apparatus. For example, the process 400 can be implemented by the computer system 102. At 402, medical imaging data associated with a patient can be received from a client device 116. The medical imaging data can include an image object, one or more data objects related to the image objects, and metadata associated with the patient. The image object and the one or more data objects are encoded in Digital Imaging and Communication in Medicine (DICOM) format. The metadata includes personal information about the patient, and time and location at which the DICOM image file was captured. Some of the metadata can be provided by a user of the client device and can be received separately from the DICOM data. Some of the metadata can be received as part of the DICOM data and can be extracted.

At 404, the received metadata can be compared with existing metadata associated with multiple existing patients. The existing metadata is stored in a database. Based on a result of the comparing, at 406, a subset of the multiple existing patients can be identified as a potential match with the patient. At 408, the subset can be provided, for example, for display on a display device connected to the computer system 102 or the server computer system 108. A selection of an existing patient from among the subset can be requested. At 410, input selecting an existing patient can be received. At 412, the medical imaging data including the image object, one or more data objects related to the image objects and the metadata can be provided to be associated with the existing patient.

In some situations, it can be determined that no existing patient in the database is a potential match with the patient based on the result of the comparing. In response, a new patient record can be generated using a HL7 ADT A04 patient registration message or electronic health record system specific web services call. The medical imaging data including the image object, one or more data objects related to the image objects and the metadata can be provided to be associated with the new patient record.

The metadata can include a first name, a last name, a sex, and a date of birth of the patient. Based on the result of the comparing, it can be determined that a first name, a last name, a sex, and a date of birth of an existing patient in the database matches the first name, the last name, the sex, and the date of birth, respectively, of the patient. In response, the medical imaging data including the image object, one or more data objects related to the image objects and the metadata can be provided to be associated with the existing patient by generating either an HL7 ADT A24 link patient information message or an HL7 ADT A40 merge patient message.

Implementations of the subject matter and the operations described in this disclosure can be implemented in digital electronic circuitry, or in computer software, firmware, or hardware, including the structures disclosed in this disclosure and their structural equivalents, or in combinations of one or more of them. Implementations of the subject matter described in this disclosure can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, for example, a machine-generated electrical, optical, or electromagnetic signal that is generated to encode information for transmission to suitable receiver apparatus for execution by a data processing apparatus. A computer storage medium, for example, the computer-readable medium, can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical and/or non-transitory components or media (for example, multiple CDs, disks, or other storage devices).

In some implementations, the operations described in this disclosure can be implemented as a hosted service provided on a server in a cloud computing network. For example, the computer-readable storage media can be logically grouped and accessible within a cloud computing network. Servers within the cloud computing network can include a cloud computing platform for providing cloud-based services. The terms "cloud," "cloud computing," and "cloud-based" may be used interchangeably as appropriate without departing from the scope of this disclosure. Cloud-based services can be hosted services that are provided by servers and delivered across a network to a client platform to enhance, supplement, or replace applications executed locally on a client computer. The system can use cloud-based services to quickly receive software upgrades, applications, and other resources that would otherwise require a lengthy period of time before the resources can be delivered to the system.

The operations described in this disclosure can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, for example, an FPGA (field programmable gate array) or an ASIC (application-specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub-programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of non-volatile memory, media and memory devices, including by way of example semiconductor memory devices, for example, EPROM, EEPROM, and flash memory devices; magnetic disks, for example, internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this disclosure can be implemented on a computer having a display device, for example, a CRT (cathode ray tube) or LCD (liquid crystal display) monitor, for displaying information to the user, and a keyboard, a pointing device, for example, a mouse or a trackball, or a microphone and speaker (or combinations of them) by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this disclosure can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this disclosure, or any combination of one or more such back-end, middleware, or front-end components. The components of the system can be interconnected by any form or medium of digital data communication, for example, a communication network. Examples of communication networks include a local area network ("LAN") and a wide area network ("WAN"), an inter-network (for example, the Internet), and peer-to-peer networks (for example, ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (for example, an HTML page) to a client device (for example, for purposes of displaying data to and receiving user input from a user interacting with the client device). Data generated at the client device (for example, a result of the user interaction) can be received from the client device at the server.

While this disclosure contains many specific implementation details, these should not be construed as limitations on the scope of any implementations or of what may be claimed, but rather as descriptions of features specific to particular implementations of particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A system comprising:
   data processing apparatus; and
   a computer-readable medium storing instructions executable by the data processing apparatus to perform operations comprising:
     establishing a connection, between the data processing apparatus and a client device associated with a local medical imaging system which is configured to acquire and store medical imaging data associated with a patient, wherein the medical imaging data includes an image object, one or more data objects related to the image objects, and metadata associated with the patient, wherein the image object and the one or more data objects are encoded in Digital Imaging and Communication in Medicine (DICOM) format, wherein the metadata includes personal information about the patient, and time and location at which the DICOM image file was captured;
     in response to establishing the connection:
       dynamically downloading, onto the client device as a non-persistently installed computer software application, software components necessary to transmit the medical imaging data to the system; and
       executing, on the client device, the computer software application, wherein the executing causes a display device connected to the client device to present:
         an Internet Protocol (IP) address of the medical imaging system;
         a listening Transmission Control Protocol (TCP) port; and
         a DICOM Application Entity (AE), wherein the IP address, the TCP port, and the DICOM AE title are provided to the local medical imaging system to establish and configure a connection between the client device and the local medical imaging system;
       in response to the local medical imaging system receiving the IP address, the TCP port and the DICOM AE title, the client device functions as a medical imaging receiver configured to receive the medical imaging data from the local medical imaging system via a DICOM protocol and transmit the medical imaging data to the data processing apparatus via a protocol different from the DICOM protocol; and
     receiving the medical imaging data at the data processing apparatus from the local medical imaging system through the client device.

2. The system of claim 1, the operations further comprising:
   receiving a request for an imaging study overread from the client device, wherein an overread is a medical interpretation of an imaging study;
   determining that the patient is an existing patient; and
   upon determining that the patient is an existing patient, automatically linking the medical imaging data to the existing patient in response to receiving the request for the imaging study overread.

3. The system of claim 2, the operations further comprising:
   determining that the patient is a new patient; and
   upon determining that the patient is a new patient, generating a new patient record for the patient and automatically linking the medical imaging data to the new patient in response to receiving the request for the imaging study overread.

4. The system of claim 1, the operations further comprising:
   comparing the received metadata with existing metadata associated with a plurality of existing patients, wherein the existing metadata is stored in a Picture Archiving and Communication System (PACS);
   based on a result of the comparing, identifying a subset of the plurality of existing patients as a potential match with the patient;
   providing the subset of the plurality of existing patients;
   requesting a selection of an existing patient from among the subset of the plurality of existing patients;
   receiving input selecting an existing patient; and
   providing the medical imaging data including the DICOM image file to be associated with the existing patient.

5. A system comprising:
   a computer system comprising:
     a data processing apparatus; and
     a computer-readable medium storing instructions executable by the data processing apparatus to perform one or more operations;
   a local medical imaging system comprising a modality configured to acquire or generate medical imaging data, the modality comprising at least one of a CT scanner, a MRI scanner, an X-Ray image processor or an ultrasound machine, the medical imaging data associated with a patient, wherein the medical imaging data includes an image object, one or more data objects related to the image objects, and metadata associated with the patient, wherein the image object and the one or more data objects are encoded in Digital Imaging and Communication in Medicine (DICOM) format, wherein the metadata includes personal information about the patient, and time and location at which the DICOM image file was captured; and
   a client device associated with the local medical imaging system, wherein the one or more operations comprise:
     hosting a computer software application configured to cause the client device to function as transmitter to transmit medical imaging data;

in response to a request from the client device, establishing a connection between the client device and the computer system;

dynamically downloading, onto the client device as a non-persistently installed computer software application, software components necessary to transmit the medical imaging data to the system;

executing, on the client device, the computer software application remotely from the client device without installing the computer software application on the client device, wherein executing the computer software application causes a display device connected to the client device to present:

an Internet Protocol (IP) address of the medical imaging system;

a listening Transmission Control Protocol (TCP) port; and a DICOM Application Entity (AE) title, wherein a user of the client device inputs the IP address, the TCP port and the DICOM AE title to the local medical imaging system to establish and configure a connection between the client device and the local medical imaging system; and in response to the local medical imaging system receiving the IP address, the TCP port and the DICOM AE title, the client device functions as a medical imaging receiver configured to receive the medical imaging data from the local medical imaging system via a DICOM protocol and transmit the medical imaging data to the computer system via a protocol different from the DICOM protocol.

6. The system of claim 5, the operations further comprising:

receiving a request for an imaging study overread from the client device, wherein an overread is a medical interpretation of an imaging study;

determining that the patient is an existing patient; and upon determining that the patient is an existing patient, automatically linking the medical imaging data to the existing patient in response to receiving the request for the imaging study overread.

7. The system of claim 6, the operations further comprising:

determining that the patient is a new patient; and upon determining that the patient is a new patient, generating a new patient record for the patient and automatically linking the medical imaging data to the new patient in response to receiving the request for the imaging study overread.

8. The system of claim 5, the operations further comprising:

comparing the received metadata with existing metadata associated with a plurality of existing patients, wherein the existing metadata is stored in a Picture Archiving and Communication System (PACS);

based on a result of the comparing, identifying a subset of the plurality of existing patients as a potential match with the patient;

providing the subset of the plurality of existing patients;

requesting a selection of an existing patient from among the subset of the plurality of existing patients;

receiving input selecting an existing patient; and providing the medical imaging data including the DICOM image file to be associated with the existing patient.

9. The system of claim 5, wherein the protocol different from the DICOM protocol is a HTTPS protocol.

10. The system of claim 1, wherein the protocol different from the DICOM protocol is a HTTPS protocol.

11. A non-transitory, computer-readable medium storing instructions executable by data processing apparatus to perform operations comprising:

establishing, by a centralized system, a connection between the centralized system and a client device associated with a local medical imaging system which is configured to acquire and store medical imaging data associated with a patient, wherein the medical imaging data includes an image object, one or more data objects related to the image objects, and metadata associated with the patient, wherein the image object and the one or more data objects are encoded in Digital Imaging and Communication in Medicine (DICOM) format, wherein the metadata includes personal information about the patient, and time and location at which the DICOM image file was captured;

in response to establishing the connection:

dynamically downloading, onto the client device as a non-persistently installed computer software application, software components necessary to transmit the medical imaging data to the centralized system;

executing, on the client device, the computer software application, wherein the executing causes a display device connected to the client device to present:

an Internet Protocol (IP) address of the medical imaging system;

a listening Transmission Control Protocol (TCP) port; and a DICOM Application Entity (AE) title; and in response to executing the computer software application on the client device:

converting the client device into a medical imaging data router by providing the IP address, the TCP port, and the DICOM AE title to the local medical imaging system, wherein the IP address, TCP port, and the DICOM AE title establish and configure a connection between the local medical imaging system and the client device;

receiving, from the local medical imaging device at the client device and via a DICOM protocol, the medical imaging data; and transmitting, from the client device and over the connection between the centralized system and the client device, the medical imaging data via a HTTPS protocol.

* * * * *